United States Patent [19]

Pfeil

[11] Patent Number: 5,377,692
[45] Date of Patent: Jan. 3, 1995

[54] VIBRATING CONDOM

[75] Inventor: William Pfeil, Molokai Ag. Park, Box 317, Kaunakakai, Hi. 96748

[73] Assignee: William F. Pfeil, Kaunakakai, Hi.

[21] Appl. No.: 159,593

[22] Filed: Dec. 1, 1993

[51] Int. Cl.6 ............................................. A61F 6/04
[52] U.S. Cl. ................................. 128/844; 128/918
[58] Field of Search ............... 128/32, 24 R, 64, 38–40, 128/842, 844, 918; 604/347–353; 600/38–41; 601/150–153

[56] References Cited

U.S. PATENT DOCUMENTS

| 2,567,926 | 9/1951 | Dunkelberger | 128/844 |
| 3,495,589 | 2/1970 | Clement. | |
| 3,626,931 | 12/1971 | Bysakh. | |
| 3,900,023 | 8/1975 | McBride. | |
| 4,175,554 | 11/1979 | Gerow | 600/38 |
| 4,281,648 | 8/1981 | Rogers. | |
| 4,432,357 | 2/1984 | Pomeranz | 128/844 |
| 4,523,584 | 6/1985 | Yachia | 600/38 |
| 4,671,262 | 6/1987 | West | 600/39 |
| 4,966,166 | 10/1990 | Leffler. | |
| 4,984,582 | 1/1991 | Romaniszyn et al. | 128/844 |
| 5,082,004 | 1/1992 | Reddy | 128/844 |

FOREIGN PATENT DOCUMENTS

| 2207169 | 2/1972 | Germany. | |
| 220358 | 1/1990 | United Kingdom | 128/918 |
| 2220857 | 1/1990 | United Kingdom | 128/918 |
| 0920171 | 10/1992 | WIPO | 128/918 |

Primary Examiner—Michael A. Brown
Attorney, Agent, or Firm—Barnes & Thornburg

[57] ABSTRACT

A vibrating condom or device having an inflatable vibrating region or a self-activated vibrating region which contacts the clitoris or vaginal walls. The inflation of such vibrating region is achieved by the transport of air or fluid from a power unit while the self-activated vibrating region could be achieved by an external or imbedded power source.

23 Claims, 1 Drawing Sheet

VIBRATING CONDOM

BACKGROUND AND SUMMARY OF THE INVENTION

This invention relates to a vibrating male contraceptive device or condom wherein a vibrating region is attached to an anterior portion thereof. The device is designed to contact the clitoris and vibrate in two directions. The device can also be designed to include a vibrating ring that contacts the vaginal walls.

Contraceptives, especially condoms, serve two main purposes: (i) they prevent conception; and (ii) they prevent the spread of infection and disease. However, this invention provides another important function: it supplements the stimulation of the female partner during sexual intercourse. In other words, this invention increases the sensations felt by a woman during sexual intercourse which will prove to be quite helpful to her in matching her partner's level of sexual excitement. A goal of this invention is to assist partners in obtaining simultaneous orgasms. This device will benefit the relationship between the partners and therefore the overall family relationship.

Harmonious relationships between sexual partners are improved when mutual satisfaction during sexual intercourse occurs. Investigations indicate that marriages are strengthened when partners experience mutual satisfaction during sexual intercourse. Mutual satisfaction is heightened when female orgasm and male ejaculation occur simultaneously. However, significant problems can occur when mutual satisfaction does not exist. For example, investigations report an increase in various psychological, physical, domestic and social problems when a relationship is not mutually sexually satisfying.

The following factors are some of the reasons why partners may experience a lack of mutual satisfaction:
  (i) Females and males may require different amounts of time to achieve orgasm. In fact, a female may require a different time period to orgasm for each sexual encounter.
  (ii) Stroking movements between male and female genitals may increase the likelihood of premature male ejaculations.
  (iii) Lack of stimulation intensity of the clitoris and/or the vaginal walls may reduce the likelihood of female orgasm.
  (iv) Lack of stimulation duration of the clitoris and/or the vaginal walls may reduce the likelihood of female orgasm.

On the other hand, the following factors can contribute significantly to overcoming any lack of mutual satisfaction: vaginal walls would help to adjust the time period required of a female to achieve orgasm which would in turn help her orgasm at the same time as her male partner.
  (ii) A device that would allow a woman to experience vibratory impulses while not increasing stimulation to the male would help synchronize progress toward simultaneous orgasm.

Hence a device that increases sensations to the clitoris and vaginal walls will prove to be quite helpful in matching the male's heightened level of sexual excitement so that a female can obtain an orgasm at a similar pace and time as her male partner. This is due to the fact that prolonged vibratory impulses to sensitive areas are known to be not only pleasurable but to also increase sexual excitement and assist a female in achieving an orgasm.

A number of devices exist that are designed to supplement the stimulation of the female genitals. Some examples of patented devices are U.S. Pat. No. 4,281,648 showing an inflatable condom; U.S. Pat. Nos. 3,626,931, 3,900,023 and German Patent 2,207,169 showing a vibrator; and U.S. Pat. No. 3,495,589 showing an inflatable genital device. However, such prior developments have failed to simultaneously satisfy all of the following needs: (i) preventing conception; (ii) preventing the spread of infection and disease; and (iii) stimulating a female's genitals through the use of vibrations so that mutual satisfaction can be obtained during sexual intercourse. This invention satisfies these needs and solves the problems of the prior art.

The problem which forms the basis of this invention consists in developing a device that serves as both an effective form of contraception while also serving to stimulate the sensitive parts of female genitals during sexual intercourse through the use of vibrations so that sexual excitement can be heightened which will help ensure mutual satisfaction.

This invention contemplates attaching a vibrating mechanism to the condom skin wherein the mechanism consists of (i) an inflatable vibrating strip to make contact with the clitoris; and/or (ii) an inflatable vibrating ring to make contact with the vaginal walls. The inflation of such vibrating strip and ring is achieved through the transport of air or fluid from a power unit via a duct to the vibrating region and ring. This invention also contemplates an embodiment wherein the vibrating region is imbedded into the condom skin. The vibrating region could also consist of a temperature sensitive material that flexes when subjected to heat or other stimuli. Therefore, the vibrating regions of the ring and strip can:
  (i) be actuated by inflation and deflation through the transport of air or fluid;
  (ii) be actuated electrically, either by a small battery also embedded in the condom or by an external electric source; and
  (iii) be actuated by a temperature sensitive material that flexes when subjected to heat or other stimuli.

This invention has numerous advantages. To begin with, the vibrating portion of the condom is not positioned at the tip of the condom. Rather, the vibrating portion is positioned to contact the most sensitive areas of the female during sexual intercourse—the clitoris and/or vaginal walls. Moreover, the vibrating strip attached to, or imbedded in the condom skin, is designed to contact and vibrate the clitoris while the vibrating ring is designed to stimulate the vaginal walls.

Another advantage of this invention is that it helps each partner reach simultaneous orgasm. For example, lengthwise movement during sexual intercourse stimulates the glands portion of the penis which leads to male orgasm. A cessation of such movement suspends the progression of the orgasm. However, the vibrating condom of the instant invention would continue to stimulate the female during such cessation of movement and continue to assist the sexual progression of the female toward orgasm. Therefore, a timely suspension of movement should create a matching progression to simultaneous orgasm.

Another advantage is that the diameter of a penis-with-vibrating condom is increased which results in greater contact with the clitoris and sexual stimulation for the female. This invention should not be considered only as a therapeutic device for overcoming sexual dysfunction. It can also be used to increase the pleasure of couples already enjoying a satisfying sexual relationship. Other objects, advantages, and novel features of the present invention will become apparent from the following detailed description of the invention when considered in conjunction with the accompanying drawings.

DETAILED DESCRIPTION OF THE DRAWINGS

Figure 1:
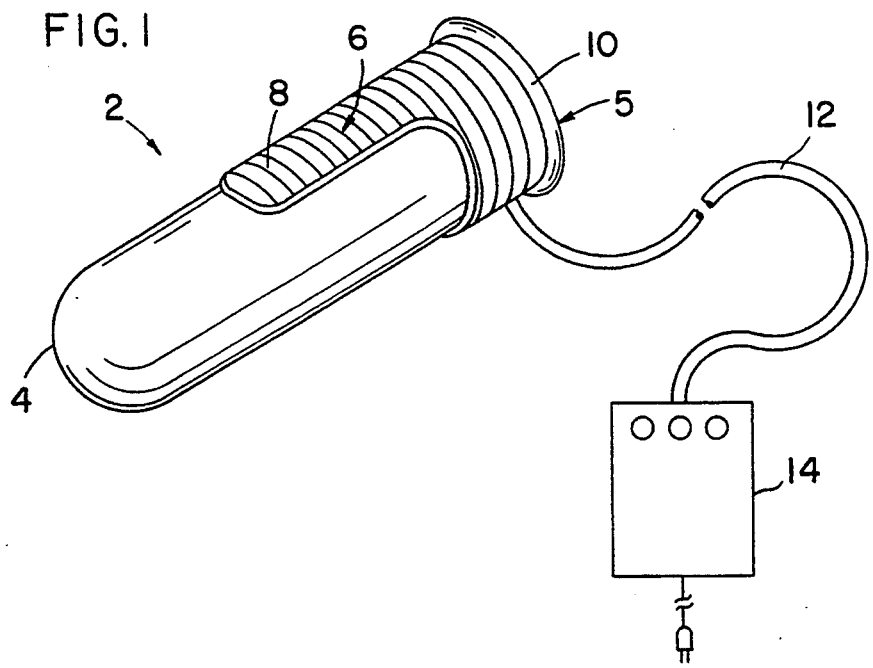
FIG. 1 is a perspective view of a vibrating condom incorporating the principles of the present invention.
Figure 2:
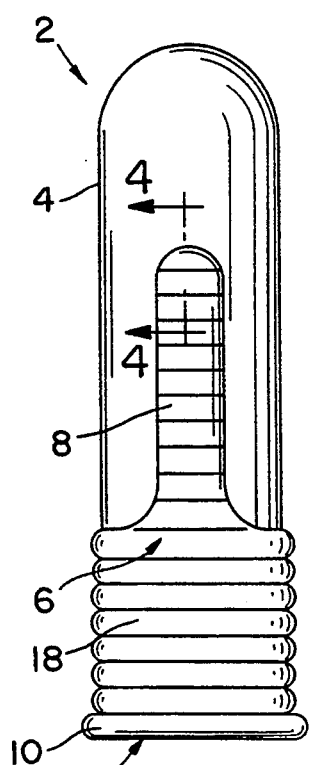
FIG. 2 shows a top view of the vibrating condom of FIG. 1.
Figure 3:
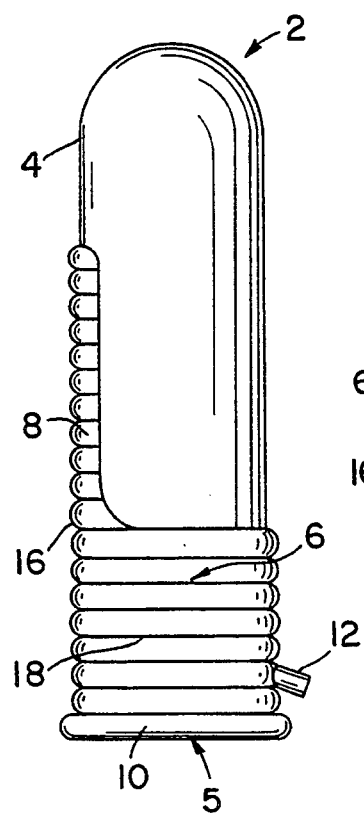
FIG. 3 shows a side view of the vibrating condom of FIG. 1.

Referring to the figures, the vibrating condom is identified generally by the numeral 2 and is illustrated in un-rolled configuration in FIGS. 1, 2, and 3. The vibrating region is generally illustrated by reference numeral 6 and is attached adjacent to the posterior portion 5 of the condom and toward the rear of the anterior portion 4 in any conventional manner such as cementing, vulcanizing, by adhesives, etc. In fact, the condom could be molded or extruded with the vibrating portion as a unitary member. In a preferred embodiment, vibrating region 6 is characterized by a strip 8 and a ring 10 which extends around the posterior portion 5 of the condom. A tube 12 is attached to both the posterior portion 5 and power unit 14 which permits inflation of the vibrating region 6. The power unit 14 has only been shown in representative outline. The power unit 14 is designed to create oscillations in pressure and may include one or more of the following features:

(i) The power unit 14 may be driven by any type of energy source: e.g. electricity, battery, spring, pneumatic, hydraulic etc.

(ii) The power unit 14 may have controls which allow the user to vary the volume of inflation, the frequency and/or amplitude and/or intensity and/or duration of the pressure oscillations.

FIGS. 1-3 show a vibrating condom 2 wherein a vibrating region 6 is attached to the posterior portion 5. The vibrating region 6 can be characterized by many possible shapes. In the embodiment illustrated in FIGS. 2 and 3, the vibrating region 6 consists of a strip 8 and a ring 10. The strip 8 is designed to contact the clitoris while the ring 10 is designed to contact the vaginal walls. The strip 8 may consist of a succession of chambers 18. FIGS. 2 and 3 shows the tube 12 which is attached to the posterior portion 5. The tube 12 transports air or fluid from the power unit 14 to the vibrating region 6. The power unit 14 creates oscillations in pressure which cause the outer skin 16 of the vibrating region 6 to vibrate.

Figure 4:
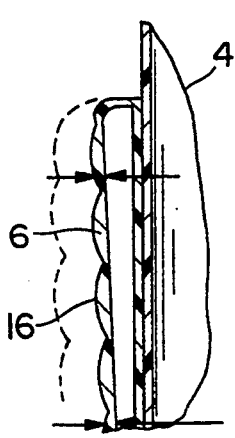
FIG. 4 shows a cross-section of the vibrating region in an inflated state.

FIG. 4 shows the vibrating region 6 in a state of inflation (dotted-lines). FIG. 4 also shows an embodiment wherein the outer skin 16 is characterized by a general decreasing of the cross sectional area from the posterior end 5 to the anterior end 4. When the power unit 14 is activated, the oscillations in pressure cause the outer skin 16 to stretch and contract lengthwise which creates a to-and-fro lengthwise vibration.

Figure 5:
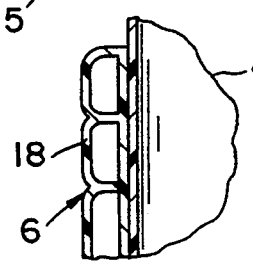
FIG. 5 shows a cross-section of the vibrating region wherein the inflated area is constructed with a succession of chambers.

FIG. 5 shows an alternative configuration of vibrating region 6 wherein the vibration region 6 is characterized by a succession of chambers 18. When the power unit 14 is activated, the oscillating pressure through the chain of chambers causes a lengthwise vibration.

Figure 6:
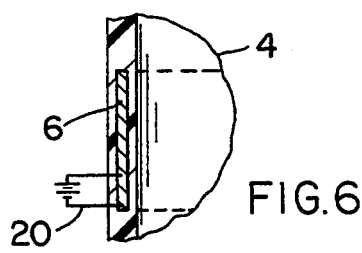
FIG. 6 shows an alternative structure wherein the vibrating region is imbedded into the condom skin and is electrically activated.

Referring now to FIG. 6, an alternative embodiment is shown wherein the vibrating region 6 is imbedded into the anterior portion 4. This embodiment does not consist of a pneumatic or hydraulic apparatus; rather, the vibrating region 6 is electrically induced to vibrate. The electrical power source 20 for this embodiment could be external to the device or embedded into the vibration region 6. For example, Nitinol is a material that can be stressed into one shape with a memory shape retained. Pulsating current flowing through the material causes the material to alternate between the stressed memory shapes to provide a vibration. Alternatively, a small vibrating reed attracted or repelled by an electro magnet could be used.

Another embodiment may include a vibrating sheet of material which includes two open ends. This embodiment would essentially be a separate vibrating device placed over the penis during sexual intercourse. This embodiment can include the same vibrating regions discussed previously. The significant difference between this embodiment and the preferred embodiment is that the two open ends permit this device to be used when a couple is trying to conceive a child. This embodiment will help stimulate the clitoris and/or the vaginal walls which will help the female partner reach simultaneous orgasm with her male partner during the act of conception.

The vibrating condom 2 of this invention can be provided in both lubricated and non-lubricated design. Moreover, as in the case of conventional condoms, the anterior portion 4 can be provided with beads or ridges projecting from such skin for greater stimulation.

Although the present invention has been described and illustrated in detail, it is to be dearly understood that the same is by way of illustration and example only, and is not to be taken by way of limitation. The spirit and scope of the present invention are to be limited only by the terms of the appended claims.

What is claimed:

1. A vibrating condom comprising:
a flexible, thin impermeable sheet material, having an open end, a closed end, and an extended length from the open end to the closed end;
vibrating means affixed to a posterior portion of the sheet material which causes said posterior portion to vibrate sensitive parts of the female genitalia; and
actuating means attached to said vibrating means for causing the vibrating means to vibrate.

2. The vibrating condom of claim 1 wherein the vibrating means is an inflatable-deflatable cavity.

3. The vibrating condom of claim 2 wherein the outer skin extends lengthwise on said anterior portion so that said outer skin vibrates outwardly and inwardly along with a lengthwise vibration.

4. The vibrating condom of claim 2 wherein the vibrating means has an outer skin in which a cross-section area decreases from one end to another end of the vibrating means.

5. The vibrating condom of claim 1 further comprising an inflatable vibrating ring positioned around the base of said condom in order to contact the vaginal walls.

6. The vibrating condom of claim 1 wherein the vibrating means has an outer skin in which a cross-section area decreases from one end to another end of the vibrating means.

7. The vibrating condom of claim 6 wherein the outer skin extends lengthwise on said anterior portion so that said outer skin vibrates outwardly and inwardly along with a lengthwise vibration.

8. The vibrating condom of claim 1 wherein the vibrating means extends lengthwise on said anterior portion so that said vibrating means vibrates outwardly and inwardly along with a lengthwise vibration.

9. The vibrating condom of claim 8 wherein the vibrating means has an outer skin in which a cross-section area decreases from one end to another end of the vibrating means.

10. The vibrating condom of claim 1 wherein the vibrating means has an outer skin which includes a plurality of chambers to permit lengthwise vibration.

11. The vibrating condom of claim 1 wherein said actuating means includes a tube wherein air or fluid can be transported from a power unit to said vibrating means.

12. The vibrating condom of claim 1 wherein the vibrating means is embedded into the condom.

13. The vibrating condom of claim 1 wherein the vibrating means is an element caused to be flexed by an electric power source.

14. The vibrating condom of claim 12 wherein the vibrating means is an element caused to be flexed by an electric power source.

15. A vibrating device comprising:
a flexible, thin impermeable sheet material having two open ends and an extended length from one open end to the other open end;
vibrating means affixed to a posterior portion of the sheet material which causes said posterior portion to vibrate sensitive parts of the female genitalia; and
actuating means attached to said vibrating means for causing the vibrating means to vibrate.

16. The vibrating device of claim 15 wherein the vibrating means is an inflatable-deflatable cavity.

17. The vibrating device of claim 15 further comprising an inflatable vibrating ring positioned around the base of said condom in order to contact the vaginal walls.

18. The vibrating device of claim 15 wherein the vibrating means has an outer skin in which a cross-section area decreases from one end to another end of the vibrating means.

19. The vibrating device of claim 15 wherein the vibrating means extends lengthwise on said anterior portion so that said vibrating means vibrates outwardly and inwardly along with a lengthwise vibration.

20. The vibrating device of claim 15 wherein the vibrating means has an outer skin which includes a plurality of chambers to permit lengthwise vibration.

21. The vibrating device of claim 15 wherein said actuating means includes a tube wherein air or fluid can be transported from a power unit to said vibrating means.

22. The vibrating device of claim 15 wherein the vibrating means is embedded into the condom.

23. The vibrating device of claim 15 wherein the vibrating means is an element caused to be flexed by an electric power source.

* * * * *